US00PP32478P2

(12) United States Plant Patent
Van Swieten

(10) Patent No.: US PP32,478 P2
(45) Date of Patent: Nov. 17, 2020

(54) ***PHALAENOPSIS* ORCHID PLANT NAMED 'PHALFATYMO'**

(50) Latin Name: ***Phalaenopsis* hybrid**
Varietal Denomination: PHALFATYMO

(71) Applicant: ANTHURA B.V., Bleiswijk (NL)

(72) Inventor: Martinus Nicolaas Gerardus Van Swieten, Utrecht (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 16/873,350

(22) Filed: Mar. 26, 2020

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 6/62
See application file for complete search history.

(56) References Cited

PUBLICATIONS

UPOV hit on *Phalaenopsis* plant named, 'PHALFATYMO', QZ PBR 50586, published Dec. 12, 2017.*

* cited by examiner

*Primary Examiner* — Anne Marie Grunberg
(74) *Attorney, Agent, or Firm* — Jondle & Associates, P.C.

(57) ABSTRACT

A new and distinct variety of *Phalaenopsis* plant named 'PHALFATYMO', particularly characterized by dark purple-red flowers with white edges and dark red lips, many branches, weak curvature of the lateral lobe, and is propagated by meristem tissue culture, is disclosed.

3 Drawing Sheets

Genus and species: *Phalaenopsis* hybrid.
Variety denomination: 'PHALFATYMO'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALFATYMO'.

The new *Phalaenopsis* plant is a product of a planned breeding program conducted by the inventor in Bleiswijk, the Netherlands. The objective of this breeding program was to create a new *Phalaenopsis* plant with many branches and attractive dark purple-red flowers with white edges and dark red lips, suitable for potted plant production.

The new *Phalaenopsis* plant 'PHALFATYMO' is a result of cross-pollination made by the inventor in December 2007 in Bleiswijk, the Netherlands, of the proprietary female, or seed parent, *Phalaenopsis* hybrid '01-1789' (unpatented) with the proprietary male, or pollen parent, *Phalaenopsis* hybrid 'PHALDOMEO' (U.S. Plant Pat. No. 25,682).

The new *Phalaenopsis* was selected by the inventor as a single plant within the progeny of the stated cross-pollination in a controlled greenhouse in Bleiswijk, the Netherlands, in December 2010. Asexual reproduction of the new *Phalaenopsis* plant by meristem tissue culture since 2013 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Sep. 26, 2017, by Applicant who obtained the subject matter disclosed directly from the inventor. 'PHALFATYMO' has not been made publicly available or sold anywhere in the world prior to the effective filing date of this application with the exception of sales or disclosures made one year or less before the effective filing date of this claimed invention by Applicant who obtained 'PHALFATYMO' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHALFATYMO' as a new and distinct variety of *Phalaenopsis* plant:

1) Dark purple-red flowers with white edges and dark red lips;
2) Plant has many branches; and
3) Weak curvature of the lateral lobe.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 42-week-old plants in February 2020. Colors in the photographs may differ from the color values cited in the detailed botanical description, which accurately describe the actual colors of the new variety.

DESCRIPTION OF THE NEW VARIETY

Figure 1:
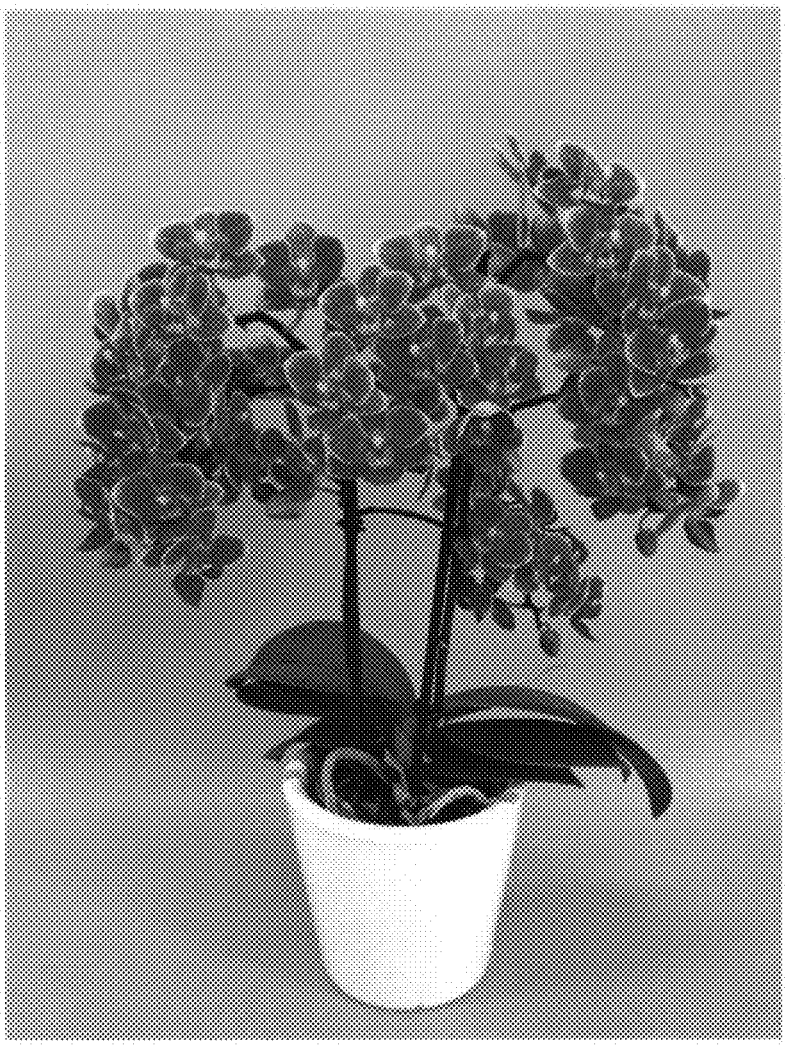
FIG. 1 shows the overall plant habit, including blooms, buds, and foliage of 'PHALFATYMO'.
Figure 2:
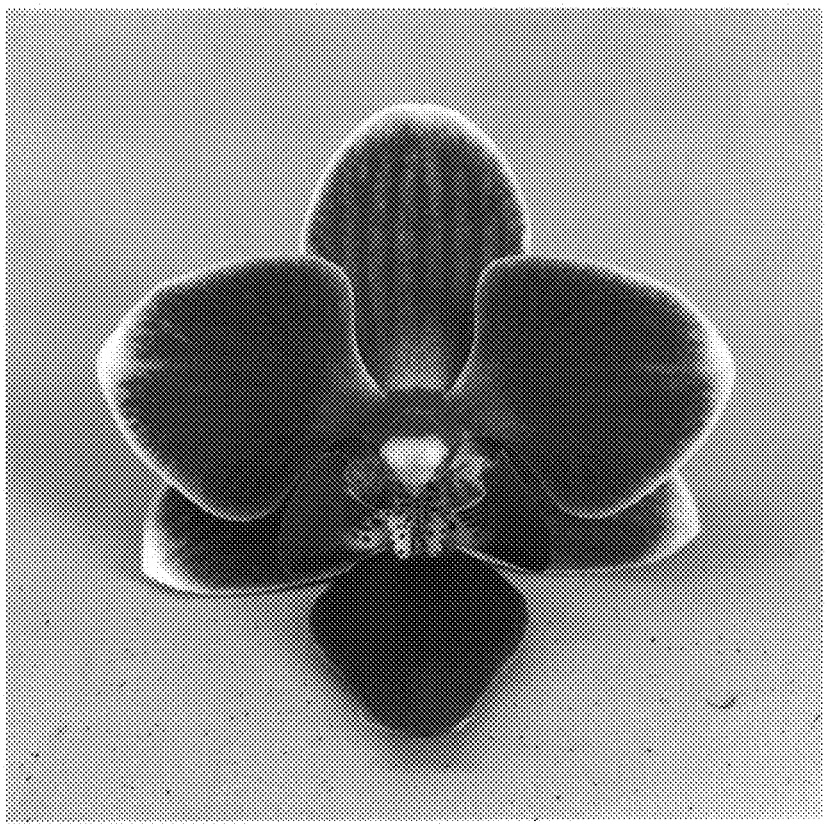
FIG. 2 shows a close-up of a flower of 'PHALFATYMO'.
Figure 3:
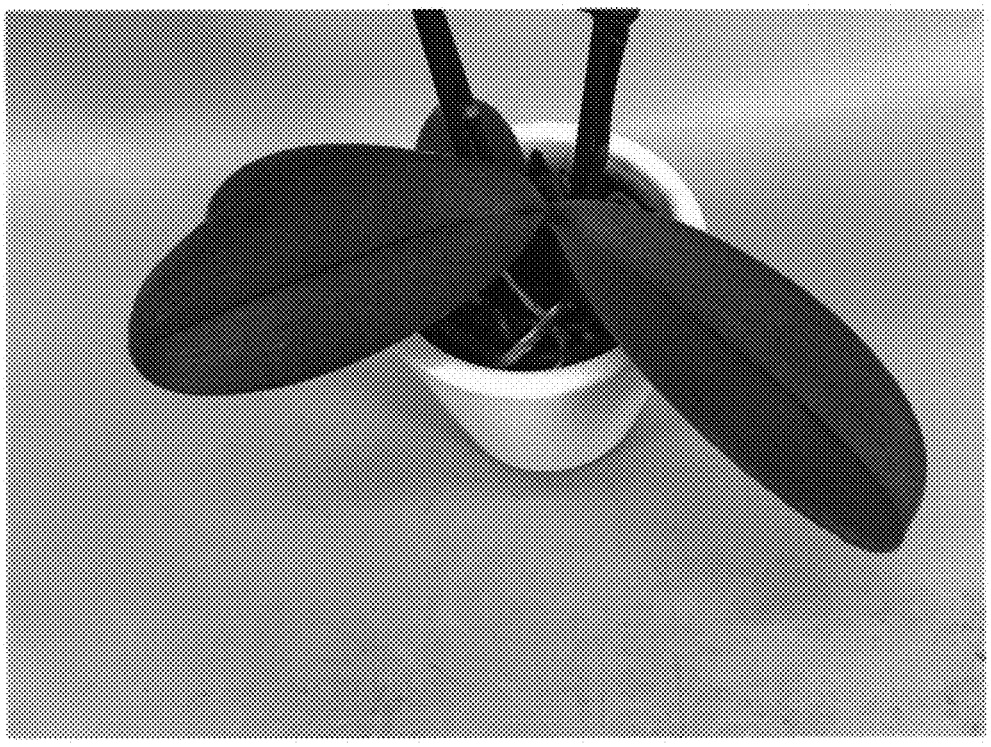
FIG. 3 shows an overhead view of the leaves of 'PHALFATYMO'.

The following detailed description sets forth the distinctive characteristics of 'PHALFATYMO'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in February 2020 on flowering plants which were planted in 9-centimeter (diameter) pots. After in vitro propagation, the plants were grown in nursery trays for 18-20 weeks, followed by transplantation to 9-centimeter pots and grown in a greenhouse between 27° C. to 29° C. for 25 weeks, continued by a cooling period of 6 weeks between 18° C. to 20° C. and 11 weeks in a greenhouse of 21° C. Flowering occurs after 42 weeks in 9-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALFATYMO'.

Parentage:

*Female parent*.—*Phalaenopsis* cultivar '01-1789' (unpatented).

*Male parent*.—*Phalaenopsis* cultivar 'PHALDOMEO' (U.S. Plant Pat. No. 25,682).

Propagation:

*Type*.—Meristem tissue culture.

Roots:

*Root description*.—Greyed-green (something between RHS 190B and 190C) colored roots with branching lateral roots having yellow-green (RHS 145B) colored root tips with a hint of purplish-red (RHS N77B).

Plant:

*Commercial crop time to flowering*.—Following asexual propagation (in vitro), the rooted cuttings grow for 18-20 weeks. After transplantation into 9-cm pots, the plants are finished after 40 to 42 weeks.

*Height (from soil level to top of inflorescence)*.—Approximately 30.0 cm to 35.0 cm.

*Width (measured from leaf tips)*.—About 22.0 cm to 24.0 cm.

*Vigor*.—Strong.

Leaves:

*Mature leaves*.—Quantity per plant: 7 to 8 leaves are produced before flowering. Length (fully expanded): 14.0 cm to 16.0 cm. Width: 5.0 cm to 6.0 cm. Position of the broadest part of the leaf: Toward the apex. Shape: Obovate. Base shape: Moderately elongated. Apex: Unequal obtuse. Leaf blade angle with the petiole (measured from the horizontal position): Between 10 degrees and 25 degrees. Leaf margin: Entire. Color: Upper surface: RHS 146A. Lower surface: RHS 146B. Texture (both upper and lower surfaces): Smooth. Thickness: 2.0 mm to 3.0 mm. Variegation: Absent. Venation: Pattern: Parallel. Color of the midvein: Upper surface: RHS 146A. Lower surface: RHS 146B.

Peduncle:

*Quantity per plant*.—1 to 3.

*Number of flowers per peduncle*.—24 to 30.

*Length*.—30.0 cm to 35.0 cm.

*Diameter*.—4.0 mm to 5.0 mm.

*Strength*.—Strong.

*Aspect*.—Upright to slightly pendent.

*Texture*.—Smooth.

*Color*.—Brown (RHS 200B).

*Internode length*.—2.0 cm to 3.0 cm.

Inflorescence description:

*Appearance*.—Upright to slightly pendent, panicle inflorescence with bilaterally symmetrical flowers that open in succession beginning with the lowermost flower.

*Number of inflorescences*.—1 to 3.

*Inflorescence size*.—Height (from base to tip): 150.0 mm to 190.0 mm.

*Flowering time*.—First flowers can be expected 10 to 11 months after planting in a 9-cm pot.

*Flower*.—Height: 35.0 mm to 40.0 mm. Diameter: 42.0 mm to 47.0 mm. Depth of lip: 19.0 mm to 21.0 mm.

*Flower longevity*.—On the plant: 7 to 9 weeks.

*Flower shape*.—Concave.

*Fragrance*.—Absent.

*Flower bud*.—Average size: Small to medium. Length: 14.0 mm to 16.0 mm. Width: 7.0 mm to 9.0 mm. Shape: Egg shaped. Color: Greenish-yellow (RHS 145B to 145C) at the base; reddish-purple (RHS N77B) toward the tip with dark purplish-red stripes (RHS N79C).

*Petals*.—Arrangement: Open/free. Shape: Semi-circular. Apex: Obtuse asymmetric. Margin: Entire. Length (from base to tip): 20.0 mm to 22.0 mm. Width: 20.0 mm to 22.0 mm. Position of the broadest part of the petal: Toward the base. Color (when fully opened): Upper surface: Basic color: Dark purple-red (something in between RHS N79C and N78A). Over color: Purplish-pink (RHS N78C) at the base and white edge (RHS NN155C). Lower surface: Basic color: Reddish-purple (RHS N78A). Over color: Reddish-purple (RHS N78B) at the middle and white edge (RHS NN155C). Number of spots and stripes on the petals (upper surface): Medium stripes. Color of spots and stripes on the petals, (upper surface): RHS N79B to N79C. Density of netting of the petals (upper surface): None. Color of the netting (upper surface): None.

*Dorsal sepal*.—Shape: Elliptic. Apex: Rounded to slightly emarginated symmetric. Margin: Entire. Length (from base to tip): 21.0 mm to 23.0 mm. Width: 16.0 mm to 18.0 mm. Position of the broadest part of the dorsal sepals: At the middle. Color (when fully opened): Upper surface: Basic color: Reddish-purple (RHS N78A). Over color: Purplish-pink (RHS N78C) at the base and white edge (RHS NN155C). Lower surface: Basic color: Purplish-pink (RHS N78C). Over color: White edge (RHS NN155C). Number of spots and stripes on the dorsal sepals (upper surface): Medium stripes. Color of spots and stripes on the dorsal sepals (upper surface): RHS N79C. Density of netting of the dorsal sepals (upper surface): None. Color of the netting: None.

*Lateral sepals*.—Shape: Ovate. Apex: Obtuse asymmetric. Margin: Entire. Length (from base to tip): 22.0 mm to 24.0 mm. Width: 15.0 mm to 17.0 mm. Position of the broadest part of the lateral sepals: Toward the base. Color (when fully opened): Upper surface: Basic color: Reddish-purple (RHS N78A). Over color: Hint of white (RHS 155B) at the base and white edge (RHS NN155C). Lower surface: Basic color: Light reddish-purple (RHS N78D). Over color: Very light purple (RHS 76C) at the base and toward margin RHS N78B. Number of spots and stripes on the lateral sepals (upper surface): Few spots at the base; medium stripes. Color of spots and stripes on the lateral sepals (upper surface): Spots RHS N78A; stripes RHS N79C. Density of netting of the lateral sepals (upper surface): None. Color of the netting (upper surface): None.

*Labellum* (*lip*).—Whiskers: Present. Length of whiskers: 1.0 mm to 3.0 mm. Color of whiskers: Dark purplish-red (RHS N79C). Pubescence on the lip: Absent.

*Lateral lobe*.—Shape: Type IV (as described in the International Union for the Protection of New Varieties of Plants (UPOV) Test Guidelines for *Phalaenopsis*); weakly spatulate. Margin: Entire. Length: 13.0 mm to 15.0 mm. Width: 8.0 mm to 10.0 mm. Color: Upper surface: White (RHS 155B) and striped RHS N79C at the base; dark purplish-red (something in between RHS N79C and N78A) toward the margin. Lower surface: White (RHS NN155B) at the base and dark purplish-red (RHS N79C) toward the margin. Number of spots and stripes on the lateral lobe: Few spots and stripes. Color of spots and stripes on the lateral lobe: RHS N79C. Density of netting of the lateral lobe: None. Color of the netting: None.

*Apical lobe*.—Shape: Broad ovate. Margin: Entire. Length: 14.0 mm to 16.0 mm. Width: 15.0 mm to 17.0 mm. Color: Upper surface: Dark red (RHS 187C) and dark purplish-red (RHS N79C) toward whiskers. Lower surface: White (RHS 155C) at the middle; reddish-purple (RHS N78A) and dark purplish-red (RHS N79C) toward wings. Number of spots and stripes on the apical lobe: None. Color of spots and stripes on the apical lobe: None. Density of netting of the apical lobe: None. Color of the netting: None. Bump and ridge: Present.

*Callus*.—Average size: Small. Height: 0.3 cm to 0.4 cm. Length: 0.4 cm to 0.5 cm. Width: 0.2 cm to 0.3 cm. Color: Light greenish-yellow (RHS 1D); dotted RHS 72A.

Reproductive organs:

*Column*.—Length: 7.0 mm to 9.0 mm. Diameter: 4.0 mm to 5.0 mm. Color: Reddish-purple (RHS N78A).

*Pollinia*.—Quantity: 2. Diameter: 0.9 mm to 1.1 mm. Color: Orange (RHS 25A).

*Ovary*.—Length: 11.0 mm to 13.0 mm. Diameter: 2.0 mm to 2.2 mm.

*Pedicel*.—Length: 30.0 mm to 32.0 mm. Diameter: 2.3 mm to 2.5 mm. Texture: Smooth. Color: Slightly brown (RHS 200C) at the base; light yellow-green (RHS 146D) and light reddish-purple (RHS N75A) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

The female parent plant of 'PHALFATYMO', cultivar '01-1789' (unpatented), is no longer in existence, therefore a meaningful comparison cannot be made.

'PHALFATYMO' differs from male parent plant 'PHALDOMEO' (U.S. Plant Pat. No. 25,682) in that 'PHALFATYMO' has rounded to slightly emarginated dorsal sepal apexes and calluses with a basic color of light greenish-yellow, whereas 'PHALDOMEO' has obtuse dorsal sepal apexes and calluses with a basic color of yellow. Additionally, 'PHALFATYMO' has longer leaves than 'PHALDOMEO'.

'PHALFATYMO' is most similar to the commercial *Phalaenopsis* plants named 'PHALFEMYM' (U.S. Plant Pat. No. 29,783) and 'PHALFUFLY' (U.S. Plant Pat. No. 31,024). 'PHALFATYMO' differs from the commercial variety 'PHALFEMYM' in that 'PHALFATYMO' has obovate leaves with obtuse apexes, whereas 'PHALFEMYM' has oblong leaves with rounded apexes. Additionally, 'PHALFATYMO' has narrower leaves and a larger lip depth than 'PHALFEMYM'.

'PHALFATYMO' differs from the commercial variety 'PHALFUFLY' in that 'PHALFATYMO' has obovate leaves and weakly spatulate lateral lobes, whereas 'PHALFUFLY' has oblong leaves and spatulate lateral lobes. Additionally, 'PHALFATYMO' has a larger lip depth than 'PHALFUFLY'.

I claim:

1. A new and distinct variety of *Phalaenopsis* plant named 'PHALFATYMO', substantially as described and illustrated herein.

* * * * *